(12) United States Patent
Connolly

(10) Patent No.: US 9,510,778 B2
(45) Date of Patent: Dec. 6, 2016

(54) TRANSDERMAL DEVICE

(75) Inventor: Patricia Connolly, Glasgow (GB)

(73) Assignee: UNIVERSITY OF STRATHCLYDE, Glasgow (GB)

( * ) Notice: Subject to any disclaimer, the term of this patent is extended or adjusted under 35 U.S.C. 154(b) by 932 days.

(21) Appl. No.: 13/698,889

(22) PCT Filed: May 19, 2011

(86) PCT No.: PCT/GB2011/000762
§ 371 (c)(1),
(2), (4) Date: Feb. 1, 2013

(87) PCT Pub. No.: WO2011/144900
PCT Pub. Date: Nov. 24, 2011

(65) Prior Publication Data
US 2014/0155703 A1    Jun. 5, 2014

(30) Foreign Application Priority Data

May 20, 2010    (GB) .................................. 1008448.1

(51) Int. Cl.
*A61B 5/145* (2006.01)
*A61B 5/053* (2006.01)
(Continued)

(52) U.S. Cl.
CPC ............ *A61B 5/145* (2013.01); *A61B 5/0531* (2013.01); *A61B 5/0537* (2013.01); *A61B 5/1477* (2013.01); *A61B 5/14532* (2013.01); *A61B 5/412* (2013.01); *A61B 10/0064* (2013.01); *A61B 2010/008* (2013.01); *A61B 2560/0412* (2013.01)

(58) Field of Classification Search
CPC ... A61B 5/145; A61B 5/14507; A61B 5/1451; A61B 5/14514; A61B 5/14532; A61B 5/68
See application file for complete search history.

(56) References Cited

U.S. PATENT DOCUMENTS 4,595,011 A    6/1986    Phillips
6,141,573 A    10/2000    Kurnik et al.
2002/0169411 A1    11/2002    Sherman et al.

FOREIGN PATENT DOCUMENTS

WO    WO 86/04680 A1    8/1986
WO    WO 94/14062 A1    6/1994
(Continued)

OTHER PUBLICATIONS

Yu, et al., "Using Skin Impedance to Improve Prediction Accuracy of Continuous Glucose Monitoring System", *Proc. SPIE* 6863, Optical Diagnostics and Sensing VIII, Feb. 20, 2008, vol. 6863, pp. 68630S-1 to 68630S-8.

(Continued)

*Primary Examiner* — Eric Winakur
(74) *Attorney, Agent, or Firm* — Alston & Bird LLP

(57) ABSTRACT

A transdermal device (10) for sensing one or more analytes in a biological fluid, the device (10) comprising a liquid or gel layer (14); a sensor (18) located in the liquid or gel layer (14) for sensing analyte in the gel layer and an outer layer (16) that is adapted to bind with or trap the one or more analytes of interest, wherein the device (10) is arranged so that in use the analyte is continuously drawn out of the liquid or gel (14) and into the outer layer (16) and the analyte concentration as a function of position across the gel/liquid has a defined profile.

25 Claims, 3 Drawing Sheets

(51) Int. Cl.
*A61B 5/1477* (2006.01)
*A61B 5/00* (2006.01)
*A61B 10/00* (2006.01)

(56) References Cited

FOREIGN PATENT DOCUMENTS

| WO | WO 95/24859 A1 | 9/1995 |
| WO | WO 99/45140 A1 | 9/1999 |
| WO | WO 00/57177 A1 | 9/2000 |
| WO | WO 2005/077260 A1 | 8/2005 |
| WO | WO 2006/007472 A2 | 1/2006 |
| WO | WO 2007/075928 A2 | 7/2007 |
| WO | WO 2009/025698 A1 | 2/2009 |

OTHER PUBLICATIONS

Intellectual Property Office, Combined Search and Examination Report for Application No. GB1008448.1, Sep. 17, 2010, 8 pages, Great Britain.
European Patent Office, International Search Report for International Application No. PCT/GB2011/000762, mailed Dec. 29, 2011, 6 pages, The Netherlands.
Sun, Ying, "Skin Absorption Enhancement by Physical Means: Heat, Ultrasound and Electricity," Transdermal and Topical Drug Delivery Systems, Jan. 1, 1997, pp. 337 to 355, XP000987211.

(a)

(b)

(c)

TRANSDERMAL DEVICE

FIELD OF THE INVENTION

The present invention relates to a transdermal device. In particular, the present invention relates to a passive transdermal device for sensing or monitoring an analyte in a biological fluid, such as glucose.

BACKGROUND OF THE INVENTION

Non-invasive techniques for medical use are of great interest, for example for glucose monitoring for diabetics, where devices for portable self monitoring are important. A great deal of research and development effort has gone into this area. In recent years a number of new sensor technologies have been explored, including transdermal sensing.

Transdermal sensing uses a sensor that is positioned on a patient's skin to sense substances, for example in the blood stream or in the interstitial fluid, through the skin. Transdermal extraction of molecules can be done using microneedles, but this involves piercing the skin, which gives opportunity for infection and/or needle breakage. Alternatively, ultrasound can be used to permeate the skin. However, this requires a more complex device, and skin is highly permeable for a short timeafterwards.

Transdermal methods which do not breach the skin or can measure through the epidermis are appealing. One such method is iontophoresis. Iontophoresis involves using a low electric current typically passed through gel electrodes to introduce ions of a medicine into tissue. This has been used for transdermal drug delivery and local anaesthetics. Reverse Iontophoresis (RI) is the term for the use of iontophoresis to extract molecules from the skin for diagnostics. RI is based on the same principle of low current passing through gel electrodes into the skin, but instead of delivery, there is an extraction of charged and uncharged molecules and ions into the gel for detection.

WO86/04680A1 describes a patch that has a moist or liquid bridge on the skin to let molecules diffuse into a material that binds the molecules. From time to time the complete system is removed from the skin and the bridge material treated or tested. The device collects an amount of the molecule of interest depending on the permeability of the skin at that time, the time of application of the patch and the starting quantities of the molecule already present in the sweat pores or on the skin. A problem with the device of WO86/04680 is that the liquid bridge suggested would not allow the amount of analyte of interest in the bridge to be instantly or continuously monitored.

WO00/057177 describes a patch that combines an outer membrane with a hydrophobic liquid bridge that is in contact with the skin to allow diffusion of an analyte, for example glucose, to the membrane. The membrane has a colour change chemistry system that reacts with the analyte in the membrane and changes colour. Thus, a glucose reading can be obtained by placing the patch on the skin, waiting and then reading the colour change on the membrane. A problem with this system is that skin bound glucose and sweat pore glucose are included in the reading and only the overall colour change related to the time period of contact of the material with the skin and the skin's permeability is provided. Thus, temporal fluctuations cannot be detected. Another problem is that the device cannot be used to continuously measure the analyte.

WO2009/025698 describes devices for collecting and analysing sweat using a sweat collection device. This has a gradient and a collection location. The gradient is configured to direct sweat toward the collection location when the sweat collection device is applied to a skin surface. This gradient is a surface energy or radial gradient that can be designed to enhance and guide the flow of sweat. The gradient is created by hydrophobic and hydrophilic patterns and guides the sweat preferentially along the hydrophilic areas. The device is dependent on sweat generation and flow and thus dependent on physiological activity or induced sweating to detect a glucose or analyte level of sweat. This is difficult to apply in practice to temporal monitoring of analyte without multiple changes of the skin patch. It is also difficult in practice to separate transdermal diffusion of analyte from sweat borne analyte for many molecules.

SUMMARY OF THE INVENTION

According to one aspect of the present invention, there is provided a transdermal device for sensing one or more analytes in a biological fluid, the device comprising a liquid or gel layer, a sensor located in the liquid or gel layer for sensing analyte flux through the gel layer and an outer layer that comprises a binding or trapping agent for binding with or trapping the one or more analytes, wherein the device is arranged so that the analyte is continuously drawn out of the liquid or gel and into the outer layer. Preferably, the liquid/gel layer is substantially uniform.

By providing a binding or trapping agent in the outer layer for continuously drawing the analyte out of the liquid or gel, there is provided a mechanism for controlling analyte diffusion through the device and ensuring that the analyte moves into the outer layer. This avoids a build up of the analyte in the liquid/gel layer, and controls the diffusion pattern. This means that an accurate measure of temporal fluctuations through the liquid/gel layer can be determined.

The binding/trapping agent may be distributed over at least over an area corresponding to the area of the gel or liquid layer, and preferably over most of the outer layer.

The binding/trapping agent may comprise one or more proteins that strongly bind analytes of interest, such as for example Concavalin A, which binds glucose.

The binding/trapping agent may comprise binding/trapping molecules, for example antibodies. For example, an anti-analyte antibody layer could be used as an alternative to bind analyte in the outer layer.

The binding/trapping agent may be a polymer that strongly binds biological molecules or ions such as nylon, nitrocellulose or other polymer layers.

The binding/trapping agent may be any material that strongly binds biological molecules, such as charcoal or porous carbon.

The outer binding/trapping layer is adapted to create a permanent and uniform diffusion profile from the skin to the outer layer of the patch.

The device may be arranged to allow diffusion of the analyte in a direction substantially perpendicular to the gel/liquid and outer layer Included in the gel/liquid layer may be a measurement device for continuously monitoring substances such as glucose, lactate, potassium, hormones, vitamins, amino acids etc. This device may be wirelessly operated and have no need of on-board power or may be powered by a small electronics patch attached to the device.

The gel layer may have a thickness preferably in the range 10 μm to 1000 μm.

The surface area of the device may preferably be in the range 1 $cm^2$ to 10 $cm^2$.

The device may be passive, that is it may collect the analyte by allowing it to diffuse into the gel without requiring a separate energy source, such as electrical current, to drive the analyte from the skin into and through the gel.

The device may be active and may include means for enhancing permeability of a patient's skin and/or transport of an analyte through the skin.

The device may include means for applying a current and/or means for applying acoustic energy to the patient's skin.

The device may include means to physically pierce a patient's skin such as one or more needles.

The device may be arranged to ensure the concentration profile across the gel/liquid is substantially linear.

Means may be provided for using a measure of flux rate to calibrate the device.

One or more electrodes may be provided for measuring skin impedance.

According to another aspect of the invention there is provided a method for calibrating a transdermal device comprising: measuring skin impedance; measuring flux of an analyte through the skin and using the measured impedance and flux to determine internal concentration of the analyte.

The method may comprise measuring the real and/or imaginary part of the skin impedance.

The method may comprise measuring the impedance using an electrical signal that has a frequency in the range 100 Hz to 10 KHz, for example 1 kHz.

The method may comprise measuring the impedance using an electrical signal that has a voltage in the range of 10 mV to 1V, preferably 100 mV to 600 mV, for example 500 mV.

The method may comprise measuring skin impedance as a function of time.

The method may comprise using the measured skin impedance to calibrate the internal concentration of the analyte.

BRIEF DESCRIPTION OF DRAWINGS

Various aspects of the invention will now be described for the purpose of example only and in conjunction with the accompanying drawings, of which.

DETAILED DESCRIPTION OF DRAWINGS

Figure 1:
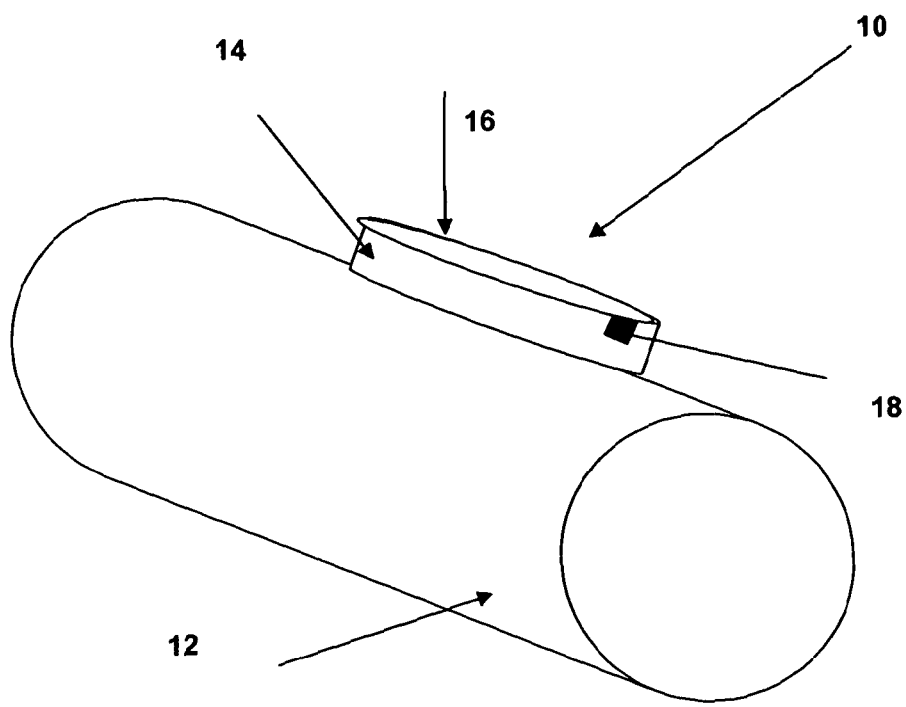
FIG. 1 shows a transdermal device on a human forearm.

FIG. 1 shows a passive transdermal device 10 on the forearm of a patient 12. This has a layer of gel 14 with a backing layer 16 directly in contact with it. The backing layer 16 acts to control the diffusion of analyte through the gel 14. The outer layer 16 has a high binding/trapping capacity and surface area to capture all transported molecules, and so preferably is porous over a large part of its structure. The gel layer 14 is substantially uniform both chemically and physically, so that it does not itself create a diffusion gradient, but instead presents a uniform environment through which analyte can flow naturally. The gel 14 can be any of a range of suitable skin contacting gels and can contain permeability enhancers which speed up the transfer of the analyte from the skin to the gel patch. For example, the gel layer 14 may comprise a methyl cellulose powder dissolved in a physiological saline or buffer to form a gel. During the fabrication of the methyl cellulose gel, a skin permeability enhancer may be added such as ethanol. Combinations of hydrophobic or hydrophilic gels and skin permeation enhancers may be combined in suitable quantities for the gel bridge.

The gel layer 14 is preferably thin or low volume to concentrate the analyte more quickly and help keep the diffusion profile uniform. Typically, gel thicknesses vary from 10 µm to 1000 µm for an ideal response. The surface area can be large or small in the devices, but for most practical patient applications, the surface area will be in the range of 1 cm$^2$ to 10 cm$^2$. The gel of FIG. 1 contains an embedded biosensor system 18 for continuously monitoring substances such as glucose, lactate, potassium, hormones, vitamins, amino acids etc. For example, placing a small, electrochemical, printed glucose or lactate sensor in the gel allows for the accurate monitoring of transdermal lactate or glucose flux, i.e. concentration as a function of time. Such printed sensors are well known to those skilled in the art of biosensor fabrication. This device may have a wireless transmitter for sending sensed data to a remote location and a processor for analysis and display, if needed. The device may be wirelessly operated and may have no need of on-board power. In this case, an electromagnetic signal to an antennae powers on device electronics to control and report from the device. Alternatively, a small battery and electronics may be attached to power the device.

Figure 2:
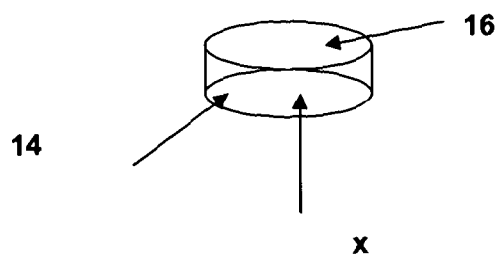
FIG. 2 is a diagram showing the key components of the device of FIG. 1, before addition of a biosensor.

Alternatively, the gel could contain substances which cause a colour change after a certain time related to the flux level of a substance of interest such as glucose, vitamin C etc, in which case a biosensor would not be needed, as shown in FIG. 2. In this case, colour sensitivity of the gel acts as a sensor. The binding/trapping layer 16 may be transparent to allow any colour change in the gel to be viewed. Alternatively, part of the binding layer may be inactive (or perforated) to allow smaller amounts of analyte to diffuse through into a colour change zone that can be viewed through any perforation or opening while still substantially controlling the diffusion flux. Thus, an expected rate of colour change against the controlled analyte flux could be calculated and used in a diagnostic capacity.

The outer backing layer 16 has molecules that bind with the analyte of interest. The outer layer is adapted to attract the analyte and so cause it to diffuse out of the gel. Thus, close to this outer layer the concentration of the analyte of interest is always low or zero in the gel. Having the outer binding/trapping layer 16 ensures that the diffusion profile of the analyte in the gel is controlled, so that the diffusion profile is well defined/predictable. By making the patch thin, the analyte concentration is relatively high. This adds to the controllability of the diffusion parameters.

In the outer layer, a wide range of binding/trapping agents may be used. These may be proteins that strongly bind the analyte(s) of interest such as Concavalin A, which binds glucose. There could be other binding/trapping molecules, for example antibodies. Thus, an anti-analyte antibody layer could be used as an alternative to bind analyte in the outer layer. Alternatively, the outer layer could be a polymer that strongly binds biological molecules or ions such as nylon, nitrocellulose or other polymer layers offer in products for molecular binding/trapping in laboratory assays. Other materials that strongly bind biological molecules can also be employed such as a charcoal or porous carbon or ion exchange or affinity assay binding/trapping agents.

Using a binding/trapping layer 16 creates a permanent and uniform diffusion profile from the skin to the outer layer of the patch. According to Fick's first law of diffusion, the diffusion rate, J, of the analyte into the gel (and thus the transdermal flux rate) is governed by $$J=DdC/dx$$

Where D is the diffusion coefficient of the analyte of interest and dC/dx is the analyte concentration gradient in the gel. D is a constant value where the medium of transport is substantially uniform both chemically and physically.

If the outer layer binds the analyte to it (causing a local concentration of zero or near zero) then dC/dx can be re-written as $$dC/dx=(Cskin-0)/x$$

Where CSkin is the concentration of the analyte at the skin barrier and x is the thickness of the gel.

Cskin of the analyte is related to the interstial or blood concentration for molecules and ions of medical interest. Thus, if the blood or interstitial level varies, and there is a good, controlled diffusion profile, then Cskin will vary and the diffusion flux J and the profile of the analyte in the skin will change.

The biosensor 18 monitors the analyte diffusion profile through the gel layer 14. From the levels of analyte recorded, the transdermal flux from the skin can be calculated. This allows the internal (in vivo) dependence of the analyte to be directly measured. The placement of the biological sensor 18 utilises the uniformity of the diffusion profile and optimises the measurement conditions. In practice, typically the biosensor 18 is placed in the gel layer 14 but close to the skin with the outer binding/trapping layer 16 behind the sensor 18. The sensor 18 disturbs the local diffusion gradient of the analyte, but this is a regular and knowable perturbance to the diffusion gradient and can be calibrated against the different flux levels (and consequently) in vivo concentrations of the analyte.

In use, analyte diffuses through the skin and into the gel where it diffuses in a controlled manner toward the binding/trapping layer. The direction of diffusion is substantially perpendicular to the binding/trapping layer. The presence of the binding/trapping layer means that the gel is continuously having the historic transdermal analyte flux swept away into the binding/trapping outer layer. Thus, the analyte profile in the gel has a temporal, not a historical, dependence. The biosensor 18 measures the analyte concentration in the gel 14 as a function of time. In practice, the measurements are not taken immediately after the patch is applied, but instead after a short delay. This ensures that misleading quantities of the analyte, related to outer skin or pore presence of the analyte, are removed and a true in vivo dependent reading is obtained. For most parameters the interval between measurements will be in the range of 1 minute to 20 minutes.

Figure 3:
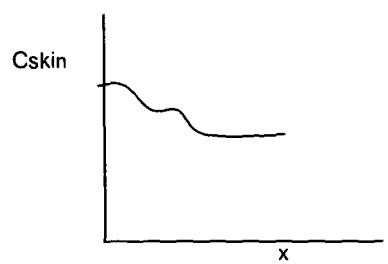
FIG. 3(a) is a graph of analyte concentration across a patch that does not have an outer binding/trapping layer to control the diffusion profile.
FIG. 3(b) is a graph of analyte concentration across a device that has an outer binding/trapping layer to control the diffusion profile.
FIG. 3(c) is a graph of the change in diffusion gradient across a patch when Cskin increases to Cskin+x due to blood of interstitial analyte concentration.
Figure 3:
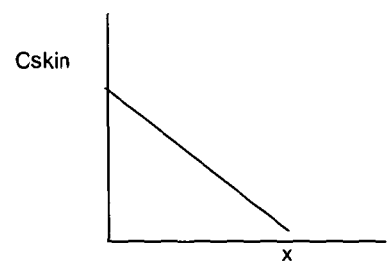
Figure 3:
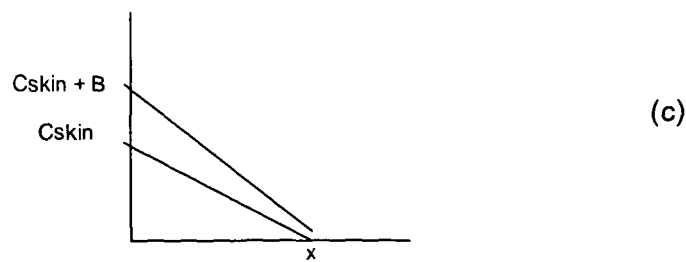

FIG. 3 shows typical concentration profiles of analyte in a gel patch after a diffusion time t in (a) a patch with no outer binding/trapping layer to control flux and (b) a patch with an outer binding/trapping layer present to control flux. Time t is >diffusion transit time for a molecule or ion of analyte to cross the patch thickness, x. From this, it can be seen that the concentration profile in the sample with no outer binding/trapping layer is variable and uncontrolled. In contrast, the concentration profile of the sample with the outer binding/trapping layer is well defined, in this case substantially linear. In FIG. 3(c), it can be seen that if the concentration of analyte in the blood or interstitial fluid increase and Cskin is increased then the diffusion gradient in the device changes. Likewise, a reduction in Cskin would be reflected in a reduced concentration gradient in the device. Such changes in the gradient can be measured by a localised biosensor 18 or colour change and can be calibrated to internal levels of analyte.

Figure 4:
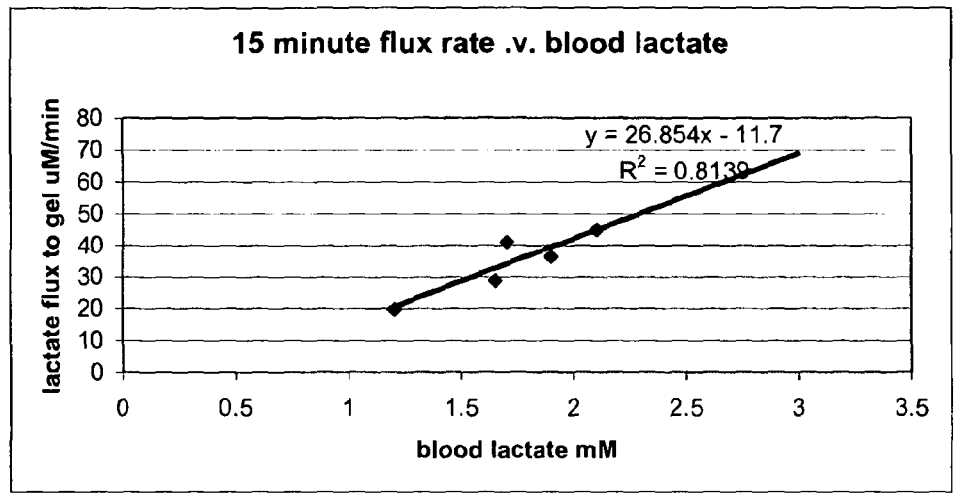
FIG. 4 is a graph of the transdermal flux calculated from an experiment on the passive diffusion of lactate from the skin into a methyl cellulose gel patch for fifteen minutes compared with the average blood lactate of each subject.

The flux rate leaving the skin and entering the patch is indicative of the interstitial fluid and/or blood concentration of an analyte. Therefore, a calculation of the flux rate is a key calibration parameter. This has been illustrated for lactate diffusion into a gel patch. The flux rate of lactate from the skin was calculated and showed a correlation with blood lactate, as in FIG. 4. Thus, the calculated flux rate in this system is a key calibration parameter that can be used alone or in a mathematical algorithm or with other useful indicators of skin permeability in the algorithm to calculate in vivo concentrations of the analyte of interest. Such permeability indicators could be the permeability coefficient of the skin or a measure of the skin impedance.

The flux rate F of an analyte leaving the skin can be considered to be proportional to both the blood or interstitial content of the analyte (or the skin bound content if that is biologically applicable), C analyte, and also to the permeability to the skin of the analyte, P analyte. Thus, an algorithm to calibrate F against internal blood may take the form $$F=kC\text{ analyte}*P\text{ analyte}+B$$

Where K and B are constants to be determined.

It is impractical in most cases to make a measurement to determine P analyte in a living subject but making a measurement of skin impedance, Z, determines important aspects of how transdermal flux flows.

Skin impedance Z can easily be determined if the device is fitted with an unobtrusive electrode system. In a preferred embodiment there is an electrode in the device and one on the skin outside the device. A simple, low voltage measurement of Z at a fixed frequency in the range 0.01 Hz-1 MHz gives a measure of complex impedance Z.

$$Z=Z'+jZ''=Z/\emptyset=Z\cos\emptyset+jZ\sin\emptyset$$

Under current flow conditions with a forcing function or potential energy V present the total current I is given by $$\begin{aligned}I &= V/Z \\ &= (V/Z)\cos-\emptyset + j(V/Z)\sin-\emptyset \\ &= I\text{ real} + I\text{ imaginary} \\ &\text{(in Electrical Engineering)}\end{aligned}$$

Where I real=water soluble flow; and I imaginary=capacitive current and lipophilic bound molecules When analyte flux flows transdermally, it takes the form of charged ions or molecules or uncharged molecules that are water soluble or lipophilic molecules that are fat soluble.

Thus, I or Z has an element of permeability measurement built in. Thus, dependent on the type of analyte, I real or I imaginary, or Z real or Zimaginary, can be part of the calibration of an individual's skin during passive or forced flux flow.

For example, for the potassium ion, it can be seen from the above that the potassium flux, which is also a current since it carries charge, should be proportional to (1/Z) cos–Ø. Additionally if Zimaginary is large this says that skin thickness, fat or capacitance may be significant and general flow of analyte will be less. Thus, in some individuals potassium flow might also be inversely proportional to the imaginary flux or current.

The driving force for potassium flux is always blood potassium concentration and so potassium flux must always be proportional to blood potassium concentration. Hence, algorithms of the format below could link potassium flux and blood concentration.

Flux of $K^+$=k (blood potassium concentration)*(1/Z) cos–Ø+B

Or for individuals with high capacitive impedance:

Flux of $K^+$=k[(blood potassium concentration)*(1/Z) cos–Ø]/((1/Z)sin–Ø)+B

Where k and B are constants to be determined.

Figure 5:
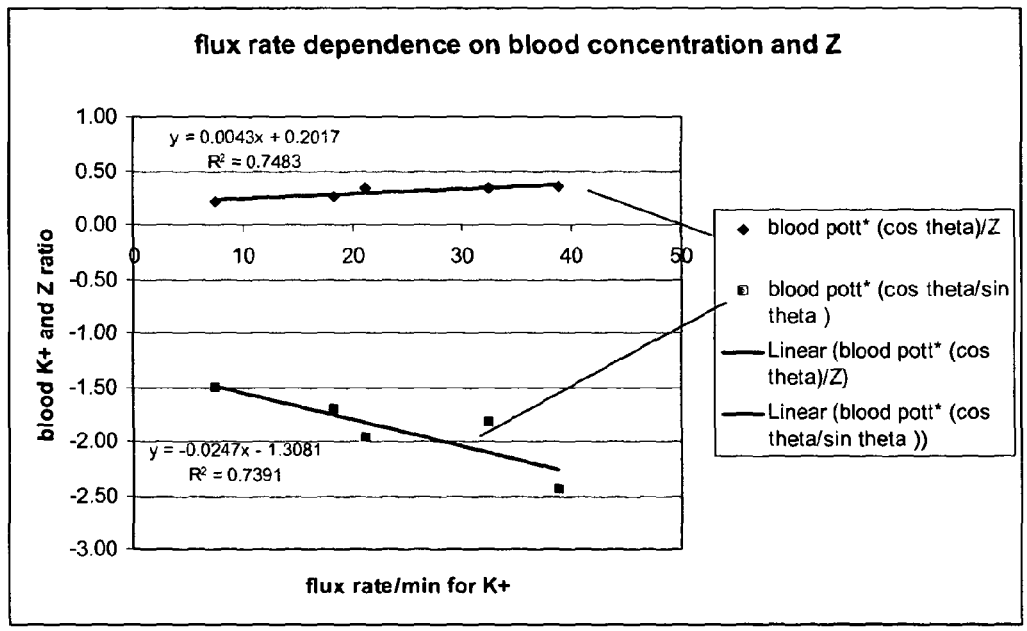
FIG. 5 is a plot of transdermal potassium flux rate into sensor patch and the ratio of blood potassium and measured skin impedance Z.

FIG. 5 shows the relationship between transdermal potassium flux rate (uM/min) into sensor patch and blood potassium and measured skin impedance, Z. This illustrates the value of such an algorithm to calibrate potassium flux to internal blood concentration and the dependence of the measured transdermal potassium flux on the blood concentration and Z. Transdermal skin impedance was measured at 500 mV, 1 KHz via the sensor patch and an external skin electrode in this experiment on five healthy volunteers. The results for all of the five volunteers are plotted in FIG. 5. The device was passive in that natural (unforced) diffusion was the transport mechanism for the potassium ion into the patch.

This algorithm and impedance method have a number of advantages. Firstly, it lets the internal blood be calculated from flux and Z without the need for blood sampling. Secondly, it links internal potassium and transdermal potassium in a mathematical manner. Potassium, sodium and chloride ions have all been suggested in the literature as potential internal standards for iontophoresis calibration or other transdermal diagnostics as, in the healthy individual, they lie in a very narrow concentration range. A practical algorithm is therefore required to link internal and external potassium.

It will be obvious to a skilled person that impedance, Z, as outlined above can be presented in many forms such as parallel skin impedance and capacitance or series skin impedance and capacitance or combinations of series and parallel circuits. The algorithms can be manipulated mathematically to reflect how these parameters are presented. For the impedance value to reflect mainly the skin impedance and not artefacts of the device, the liquid/gel layer has to be conductive. Thus, the liquid/gel from the start should comprise ions to provide high conductivity and these should be tolerable to the human body. A suitable liquid or gel would contain, for example, physiological concentrations of sodium chloride (e.g. 133 mM)

The present invention provides a simple and effective device for non-invasive monitoring of parameters in the human or animal body. Numerous different parameters could be monitored, for example potassium, sodium and chloride. These would be useful electrolyte balance parameters. Lactate and glucose combined have applications in intensive therapy and detection of onset of sepsis. Amino acids could be monitored transdermally for medical diagnostics and therapy.

A skilled person will appreciate that variations of the disclosed arrangements are possible without departing from the invention. Although the outer layer has primarily been described as including a chemical binding agent, it could take any suitable form provided the analyte of interest can be bound or trapped within it. For example, the outer layer could be a one-way membrane, such as a treated polyethersulfone membrane for ion exchange. Other polymer membranes could be used for small molecule separation from the liquid/gel by pore size of membrane or a combination of pore size, membrane charge or chemical treatment. Additionally, the use of an outer binding/trapping layer has applications on more active transdermal extraction such as microneedle, sonophoresis or reverse iontophoresis, as it improves and controls the analyte profile in the skin patch or bridge and makes results relevant temporally. Also, nanotechnology and microtechnology could be employed to miniaturise the device. Accordingly, the above description of a specific embodiment is made by way of example only and not for the purposes of limitations. It will be clear to the skilled person that minor modifications may be made without significant changes to the operation described.

The invention claimed is:

1. A transdermal device for sensing one or more analytes in a biological fluid, the device comprising a liquid or gel layer; a sensor located in the liquid or gel layer for sensing analyte in the liquid or gel layer and an outer layer adapted to bind with or trap the one or more analytes of interest, wherein the device is arranged so that in use the analyte is continuously drawn out of the liquid or gel and into the outer layer and the resulting analyte concentration as a function of position across the gel/liquid has a defined profile.

2. A device as claimed in claim 1 wherein the sensor is operable to sense analyte concentration in the gel layer as a function of time.

3. A device as claimed in claim 1 wherein the defined profile is linear.

4. A device as claimed in claim 1, wherein a binding/trapping agent is distributed at least over an area of the outer layer corresponding to a measurement area of the gel or liquid layer.

5. A device as claimed in claim 1, wherein the binding/trapping agent is distributed substantially over all of the outer layer.

6. A device as claimed in claim 1, wherein the binding/trapping agent comprises one or more proteins that strongly bind analytes of interest.

7. A device as claimed in claim 1, wherein the binding/trapping agent comprises antibodies.

8. A device as claimed in claim 1, wherein the binding/trapping agent comprises a polymer that strongly binds the analyte.

9. A device as claimed in claim 8, wherein the polymer is nylon or nitrocellulose.

10. A device as claimed in claim 1, wherein the binding/trapping agent comprises charcoal or porous carbon.

11. A device as claimed in claim 1, wherein the binding/trapping agent destorys and/or traps the analyte by chemical or biochemical means.

12. A device as claimed in claim 1, wherein outer binding/trapping layer is adapted to create uniform diffusion profile from the skin to the outer layer.

13. A device as claimed in claim 1, arranged to cause diffusion of the analyte in a direction substantially perpendicular to the gel/liquid and outer layers.

14. A device as claimed in claim 1, further comprising a measurement device for monitoring the at least one analyte, wherein the measurement device comprises the sensor.

15. A device as claimed in claim 14, wherein the measurement device measures the at least one analyte as a function of time.

16. A device as claimed in claim 1, wherein the gel layer has a thickness in the range 10 μm to 1000 μm.

17. A device as claimed in claim 1, where the liquid/gel layer is conductive.

18. A device as claimed in claim 1, wherein the surface area is in the range 1 cm$^2$ to 10 cm$^2$.

19. A device as claimed in claim 1, wherein the device is passive.

20. A device as claimed in claim 1, wherein the device is active.

21. A device as claimed in claim 1 comprising means for enhancing permeability of a patient's skin and/or transport of an analyte through the skin.

22. A device as claimed in claim 1, comprising means for applying a current and/or means for applying acoustic energy to the patient's skin.

23. A device as claimed in claim 1 comprising means to physically pierce a patient's skin.

24. A device as claimed in claim 1 comprising means for using a measure of flux rate to calibrate the device.

25. A device as as claimed in claim 1 comprising one or more electrodes for measuring skin impedance.

* * * * *